(12) United States Patent
Nakashima

(10) Patent No.: US 7,060,053 B2
(45) Date of Patent: Jun. 13, 2006

(54) SAFETY INDWELLING SYRINGE

(75) Inventor: Noboru Nakashima, Tokyo (JP)

(73) Assignee: Medikit Co., Ltd., Bunkyo-Ku (JP)

( * ) Notice: Subject to any disclaimer, the term of this patent is extended or adjusted under 35 U.S.C. 154(b) by 0 days.

(21) Appl. No.: 10/084,491

(22) Filed: Feb. 28, 2002

(65) Prior Publication Data
US 2003/0163095 A1 Aug. 28, 2003

(51) Int. Cl.
*A61M 5/32* (2006.01)
*A61M 5/00* (2006.01)

(52) U.S. Cl. ............................... 604/177; 604/263

(58) Field of Classification Search ........ 604/177–198, 604/162, 165.03, 403, 200, 232, 500, 263, 604/110, 158, 180, 171, 164.08
See application file for complete search history.

(56) References Cited

U.S. PATENT DOCUMENTS

| | | | | |
|---|---|---|---|---|
| 5,382,240 A | * | 1/1995 | Lam | 604/177 |
| 5,498,241 A | * | 3/1996 | Fabozzi | 604/177 |
| 5,676,656 A | * | 10/1997 | Brimhall | 604/165.03 |
| 5,779,679 A | * | 7/1998 | Shaw | 604/158 |
| 6,001,083 A | * | 12/1999 | Wilner | 604/263 |
| 6,197,007 B1 | * | 3/2001 | Thorne et al. | 604/263 |
| 6,659,984 B1 | * | 12/2003 | Maclean Crawford et al. | 604/263 |

FOREIGN PATENT DOCUMENTS

JP 1-136665 A 5/1989
JP 2001-259029 A 9/2001

* cited by examiner

*Primary Examiner*—Kevin C. Sirmons
*Assistant Examiner*—Roz Maiorino
(74) *Attorney, Agent, or Firm*—Smith Patent Office

(57) ABSTRACT

A safety indwelling syringe has a hollow needle to be inserted into the body of a patient, a fixed sheath fixing the hollow needle and covering the needle partly, and a protective sheath slidably fitted to the fixed sheath. The hollow needle is exposed when used. After use, the protective sheath is pulled out toward the tip of the hollow needle so as to cover the needle entirely.

7 Claims, 22 Drawing Sheets

FIG.16
FIG.17
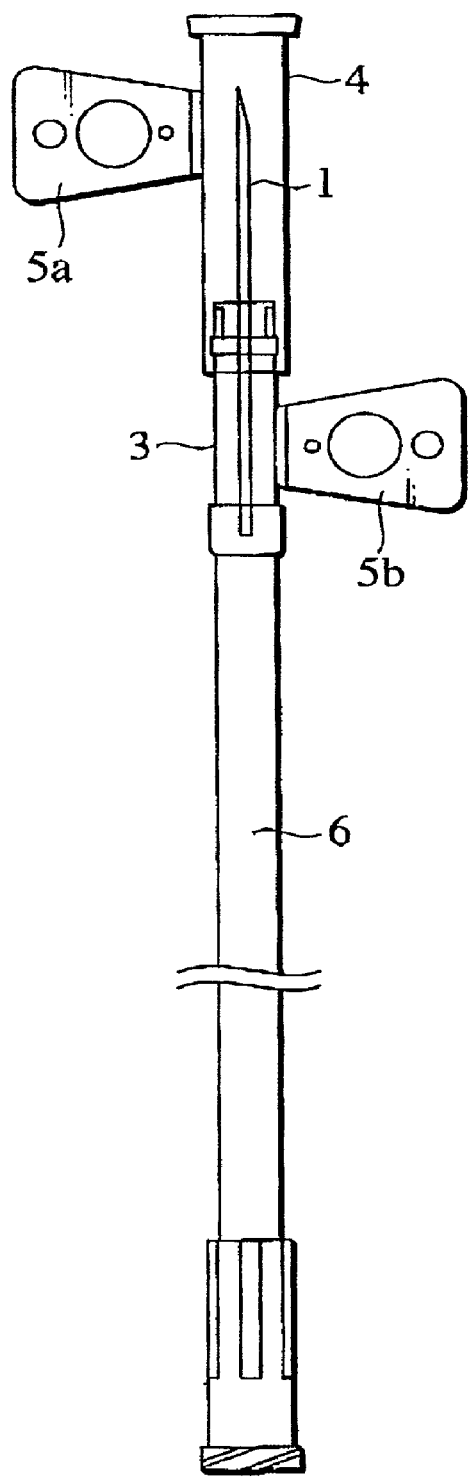
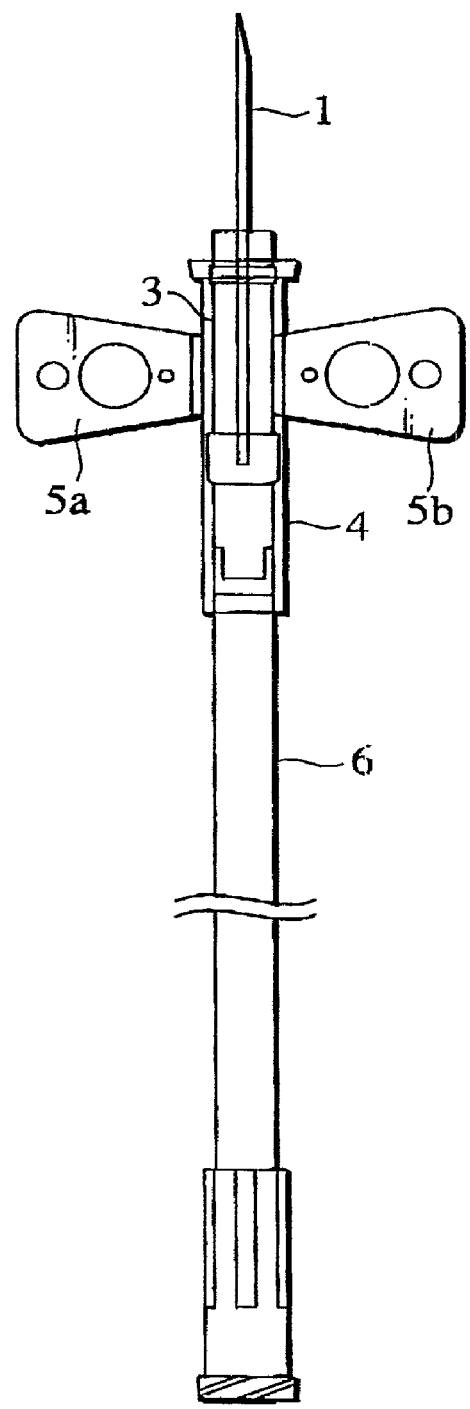

SAFETY INDWELLING SYRINGE

BACKGROUND OF THE INVENTION

1. Field of the Invention

This invention relates to a safety indwelling syringe which allows safe disposal of a hollow needle after use, and more particularly, to a safety indwelling syringe which allows safe disposal of a hollow needle by pulling out a portion of its sheath in an easy operation, housing the needle therein.

2. Description of the Related Art

An art of safely disposing hollow needles is shown in Japanese Patent Laid-Open Publication No. Hei-1-136665 disclosing a container for syringe needles. This container includes a cover plate for closing the top opening of the container body, the plate having a removal hole with a large-width portion which allows the insertion of a flange provided at a proximal end of a needle and a small-width portion which engages the flange. The hollow needle has the flange at the proximal end, and is inserted into the container through the large-width portion of the hole. The hollow needle is shifted to the small-width portion so as to engage the flange with the bottom surface of the cover plate. Then a syringe tube is pulled up, removing the hollow needle from the syringe tube to be contained in the container for disposal.

SUMMARY OF THE INVENTION

The above art requires that a container which is separate from a hollow needle be prepared for disposal of the hollow needle, and the container be always carried in using a hollow needle. However, it is often impracticable to always carry such containers for extremely busy situations in medical practices. Further, it is of concern that accidental sticking of a hollow needle into a finger may occur prior to the operation of disposing the hollow needle into the container.

This invention was made to solve the above problems, and has an object of providing a safety indwelling syringe which alone safely houses a hollow needle to be disposed of, preventing accidental sticking of the needle into a finger.

A safety indwelling syringe according to a first aspect of this invention comprises: a hollow needle to be inserted into the body of a patient; a fixed sheath fixing the hollow needle and covering the needle partly; and a protective sheath slidably fitted to the fixed sheath. The hollow needle is exposed when used. After use, the protective sheath is pulled out toward the tip of the hollow needle, covering the needle entirely.

It is thus not necessary to prepare an individual container for housing the hollow needle, which enables safe and reliable housing of the hollow needle without such a container at hand. The operation of housing the hollow needle consists only of the sliding of the protective sheath. The operation does not involve manually holding the hollow needle body or the peripheral parts or orienting the tip of the hollow needle toward fingers. This significantly reduces the possibility of accidental sticking of the hollow needle into a finger. The tip of the hollow needle, prior to use, can also be covered by the protective sheath. This prevents accidental sticks into a finger before use.

A safety indwelling syringe according to a second aspect of this invention comprises: a hollow needle to be inserted into the body of a patient; a fixed sheath fixing the hollow needle and covering the needle partly; a protective sheath slidably fitted to the fixed sheath; and a locking means for restricting the sliding movement of the protective sheath and the fixed sheath. The protective sheath is pulled out from the fixed sheath and locked, covering the hollow needle entirely.

This configuration has the locking means and has effects, in addition to the above-described effects, of reliably maintaining a state where the hollow needle is housed in the protective sheath. The tip of the hollow needle is thus prevented from being exposed with the protective sheath sliding out or returning to an original position. This prevents accidental sticking of fingers before discarding the indwelling syringe. The locking can be identified by a feel during the operation. This prevents overlooking the incomplete housing of the hollow needle.

A safety indwelling syringe according to a third aspect of this invention comprises: a hollow needle to be inserted into the body of a patient; a plurality of telescopic sheaths covering part of the hollow needle; a protective sheath being prevented from slipping out from inside the telescopic sheaths; and a flexible adapter fixed on an outer periphery of a proximal end portion of the protective sheath. When the telescopic sheaths are extended, the protective sheath covers the hollow needle entirely. The protective sheath has an elongated shape so as to be inserted into a catheter for support when the safety indwelling syringe is inserted into the catheter.

This configuration has the flexible adapter always clamping the protective sheath. When the hollow needle is pulled out from the catheter, the telescopic sheaths extend forward, and the protective sheath covers the hollow needle entirely. This effectively prevents accidental sticking of the hollow needle into fingers, which sometimes occurs when a conventional clamped catheter is used. This further eliminates a defect that a clamped portion of the conventional clamped catheter is likely to flex.

BRIEF DESCRIPTION OF THE DRAWINGS

FIG. 16 is a plan view of the safety indwelling syringe according to the third embodiment of this invention, showing the hollow needle housed in a protective sheath;

FIG. 17 is a plan view of the safety indwelling syringe according to the third embodiment of this invention, showing the hollow needle exposed for use;

DETAILED DESCRIPTION OF THE PREFERRED EMBODIMENTS

Figure 1:
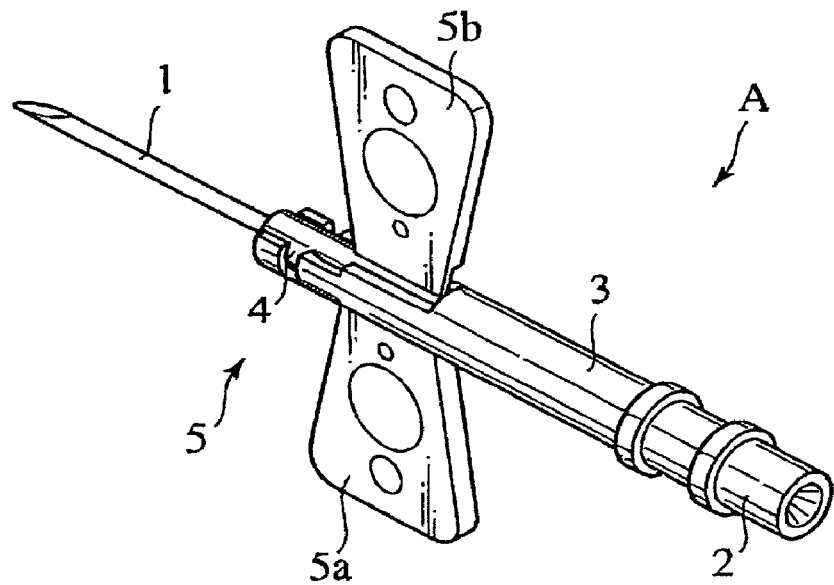
FIG. 1 is a perspective view of a safety indwelling syringe according to a first embodiment of this invention.

With reference to FIGS. 1 to 6, a first embodiment of this invention will be described. A safety indwelling syringe A according to the first embodiment of this invention has a hollow needle 1, a hub 2 fixed at a proximal end of the hollow needle 1, a fixed sheath 3 fitted to the hub 2, covering a portion of a proximal end of the hollow needle 1, a protective sheath 4 slidably fitted into the fixed sheath 3, and a pair of wings 5 protruding in opposite directions from the sheaths 3 and 4.

The hollow needle 1 is made from tough metal having good corrosion resistance such as chrome steel, for example, and is molded in a small-gauge diameter tube and then processed to an appropriate length of needle in accordance with use or purposes.

The hub 2 is fixed at the proximal end of the hollow needle 1, and is connected to an instrument via a flexible tube 6 made of resin such as soft fluoresin or polyurethane.

Figure 2:
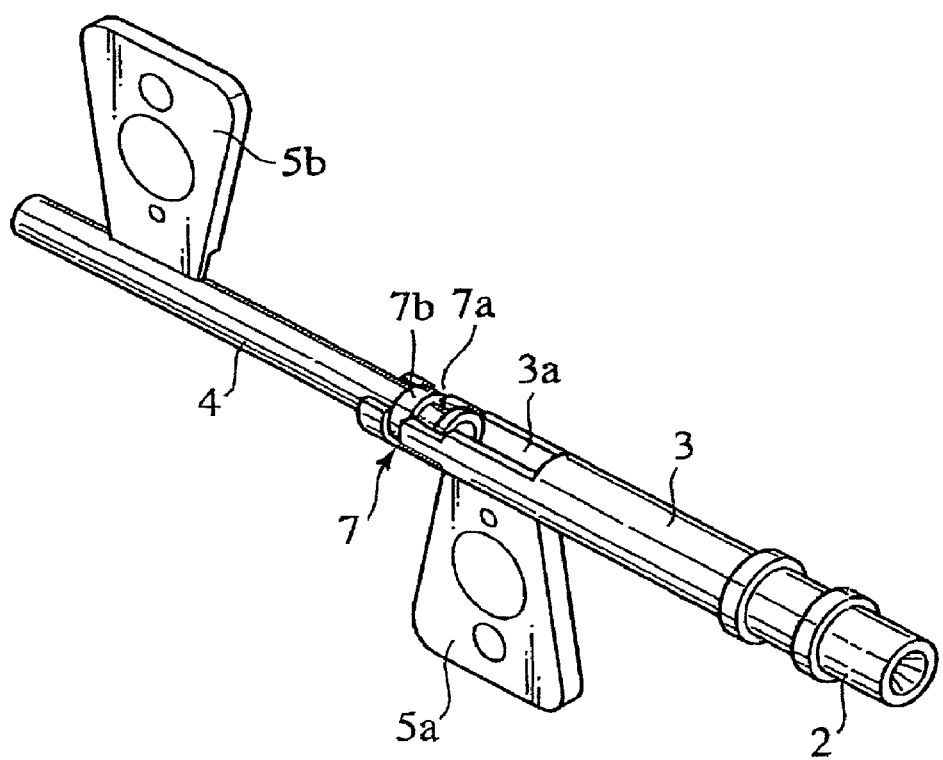
FIG. 2 is a perspective view of the safety indwelling syringe according to the first embodiment of this invention, showing a hollow needle housed in a protective sheath.
Figure 3:
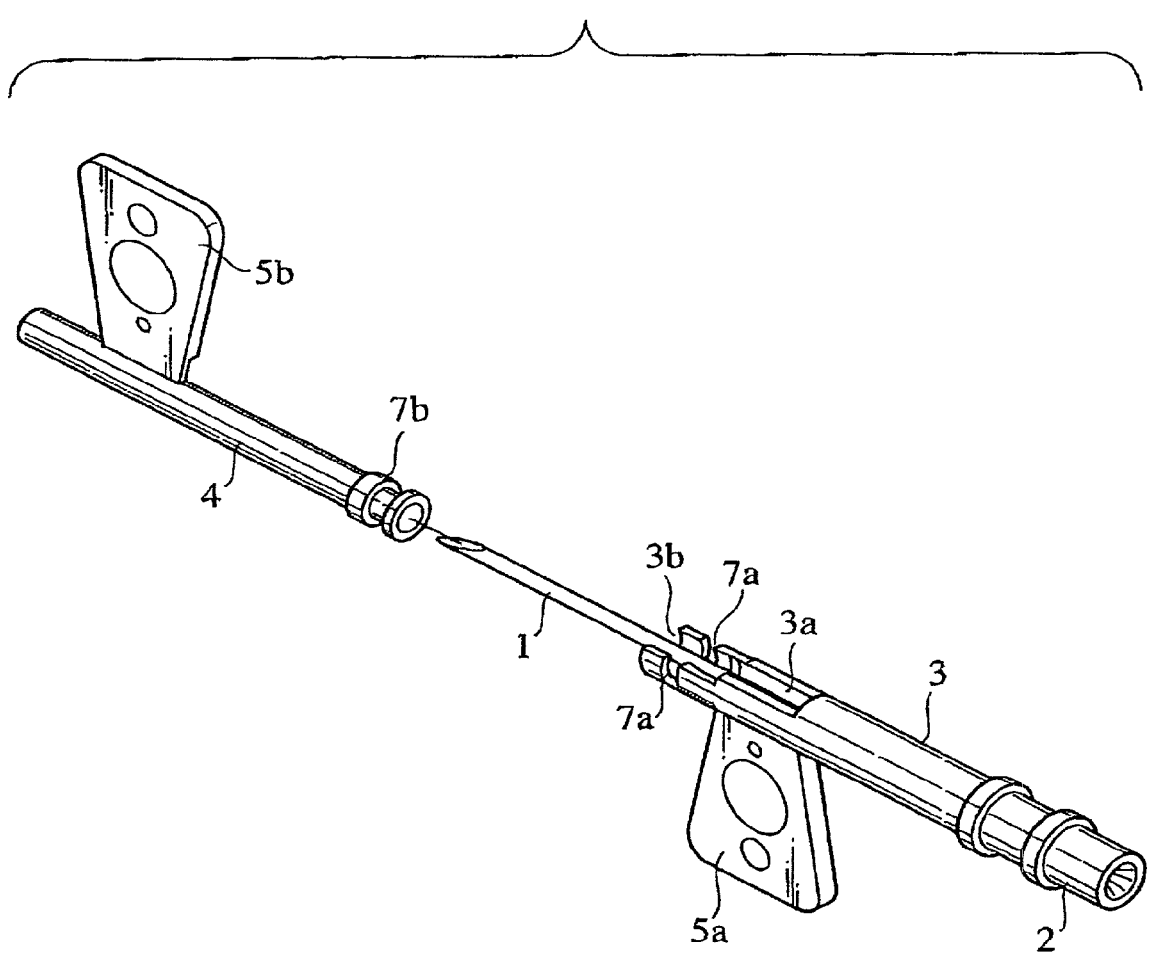
FIG. 3 is an exploded perspective view of the safety indwelling syringe according to the first embodiment of this invention.

The fixed sheath 3 is a tube with the opposite opening ends, and is formed with a slit 3a in the vicinity of its distal end as shown in FIG. 2. The slit 3a communicates with a front end opening 3b of the fixed sheath 3 for slidably accommodating a proximal portion of a second wing 5b coupled to the protective sheath 4.

A locking means 7 is provided at a front end of the fixed sheath 3 and a proximal end of the protective sheath 4 for preventing the protective sheath 4 from slipping out. The locking means 7 consists of a locking slot 7a and a guide surface 7c of a tapered surface provided in the fixed sheath 3, and a locking projection 7b protruding from an outer periphery of the protective sheath 4 to be fitted into the locking slot 7a.

The protective sheath 4 is, similar to the fixed sheath 3, a tube with the opposite opening ends, and is designed to cover the hollow needle 1 when pulled out forwardly from the fixed sheath 3 and locked.

The pair of wings 5 consists of a first wing 5a and the second wing 5b made of soft material such as resin, and is formed symmetrically with respect to the hollow needle 1. The first wing 5a is integrally coupled to the fixed sheath 3, and the second wing 5b is integrally coupled to the protective sheath 4. When the first and second wings 5a and 5b are aligned symmetrically, the hollow needle 1 is exposed. When the second wing 5b is slid in a direction to distance the wing 5b from the first wing 5a, the protective sheath 4 is pulled forwardly out from the fixed sheath 3 and covers the hollow needle 1.

Figure 4:
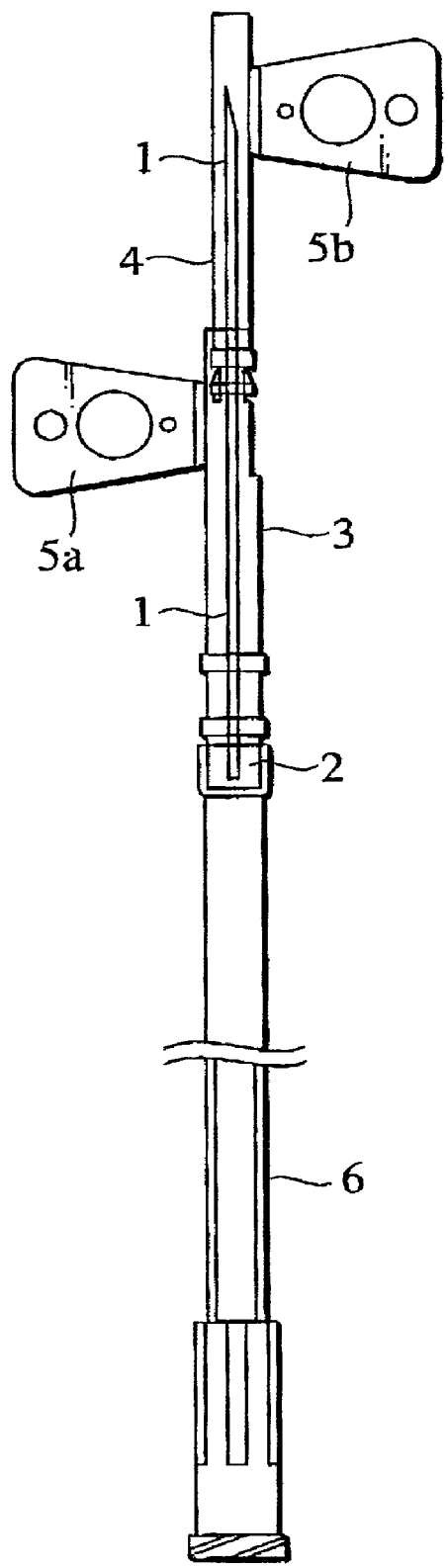
FIG. 4 is a plan view of the safety indwelling syringe according to the first embodiment of this invention, showing the hollow needle housed in the protective sheath.
Figure 5:
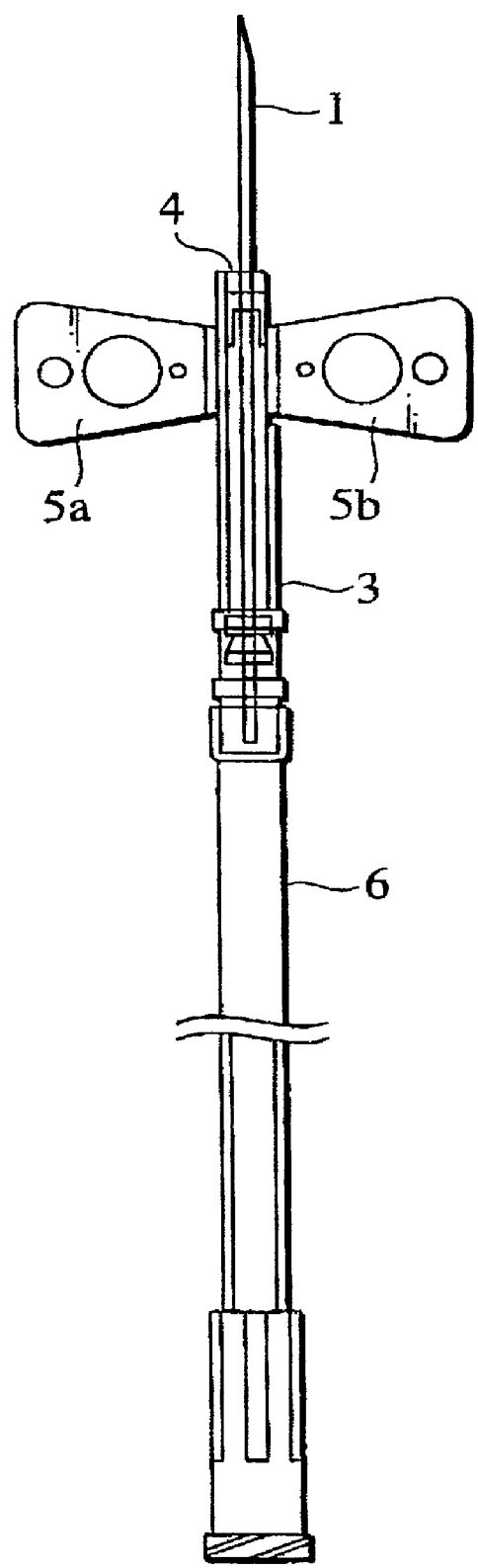
FIG. 5 is a plan view of the safety indwelling syringe according to the first embodiment of this invention, showing the hollow needle exposed for use.

The safety indwelling syringe according to the first embodiment of this invention is supplied, with the hollow needle 1 covered by the protective sheath 4 as shown in FIG. 4. In use, the hollow needle 1 is exposed as shown in FIG. 5 to be inserted into the body of a patient with the wings 5 held by an operator. After use, the second wing 5b is held to slide the protective sheath 4 forwardly or toward the tip of the hollow needle 1, housing the hollow needle 1 in the protective sheath 4, thereby enabling safe disposal without touching the body of the hollow needle 1.

Figure 6:
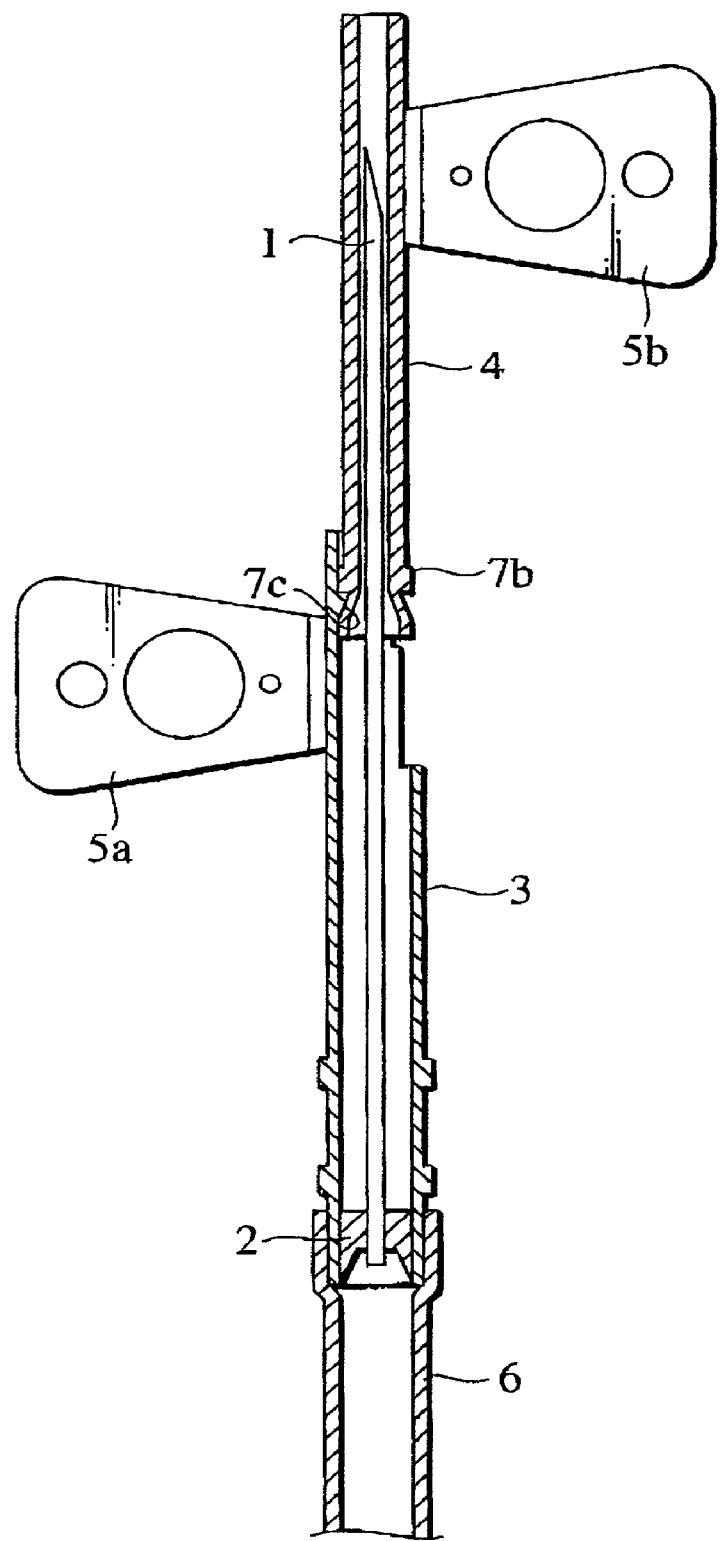
FIG. 6 is a longitudinal cross-sectional view of the safety indwelling syringe according to the first embodiment of this invention, showing the hollow needle housed in the protective sheath.

In this state, the locking projection 7b of the protective sheath 4 is engaged with the locking slot 7a of the fixed sheath 3 as shown in FIG. 6, thereby preventing the protective sheath 4 from slipping out from the fixed sheath 3. Once housed in the protective sheath 4, the hollow needle 1 is not again exposed until the engagement is intentionally released. This easily and reliably prevents accidental sticking of the hollow needle 1 into a finger.

A second embodiment of this invention will be described with reference to FIGS. 7 to 12. In these figures, elements substantially identical with those in the first embodiment are referred to by the same numerals. Different elements are referred to by new numerals.

A safety indwelling syringe B according to the second embodiment of this invention has a slide sheath 8 slidably fitted into a fixed sheath 3 in place of the protective sheath 4 in the safety indwelling syringe A of the first embodiment.

The slide sheath 8 consists of a first slide sheath 8a and a second slide sheath 8b slidably fitted into the first slide sheath 8a.

Figure 7:
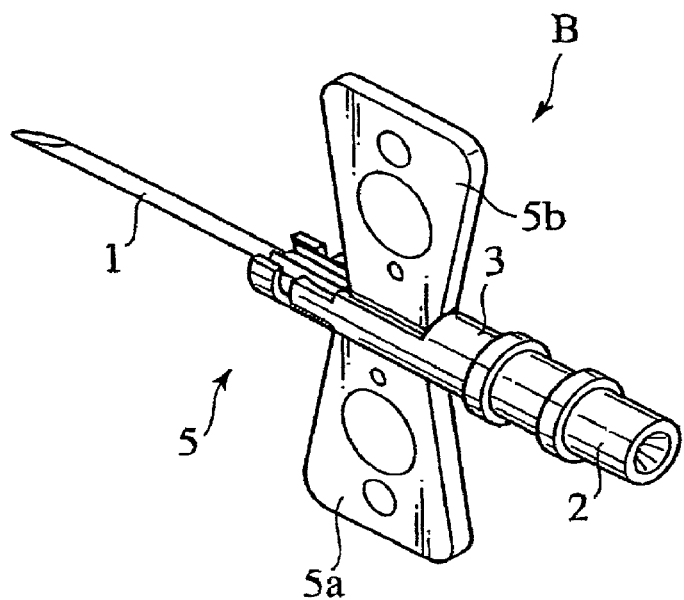
FIG. 7 is a perspective view of a safety indwelling syringe according to a second embodiment of this invention.
Figure 8:
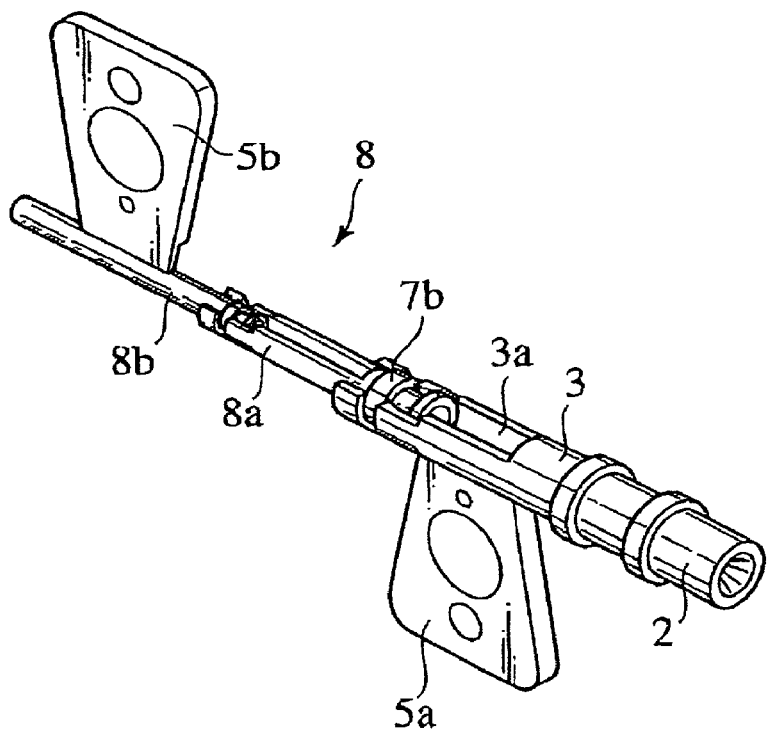
FIG. 8 is a perspective view of the safety indwelling syringe according to the second embodiment of this invention, showing a hollow needle housed in a protective sheath.
Figure 9:
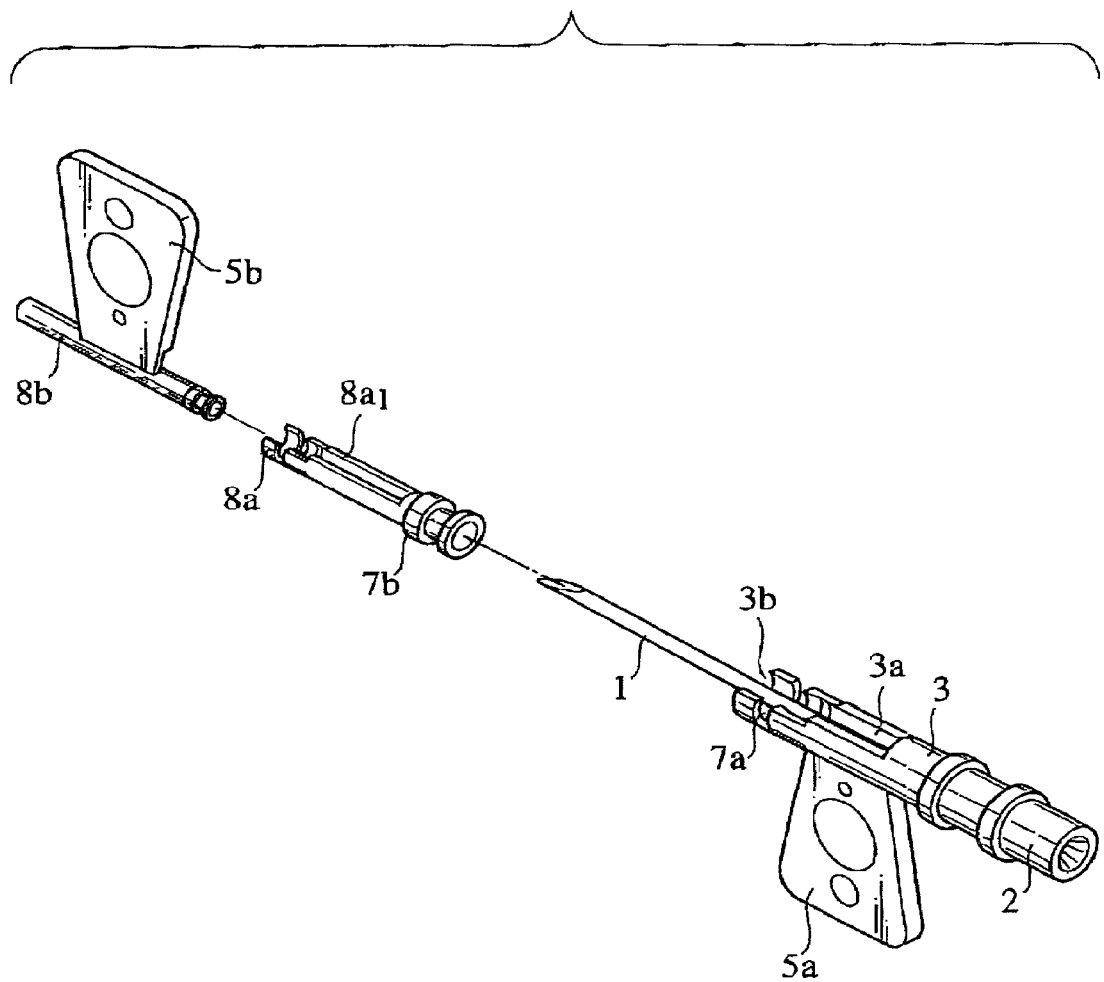
FIG. 9 is an exploded perspective view of the safety indwelling syringe according to the second embodiment of this invention.
Figure 10:
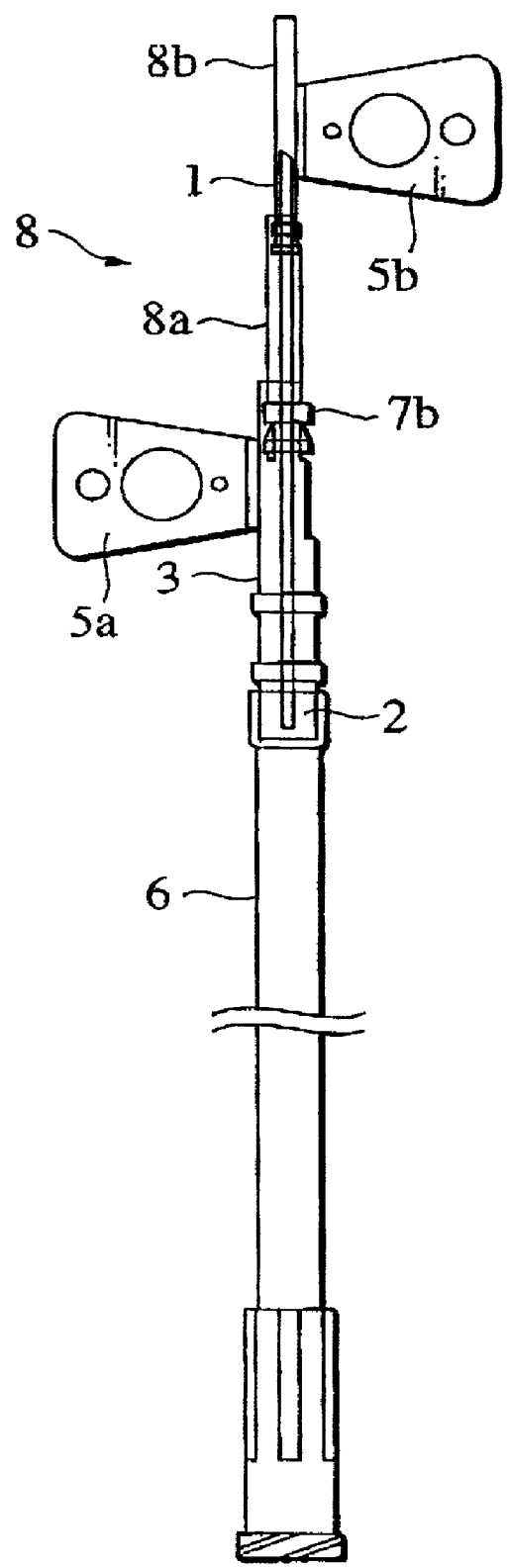
FIG. 10 is a plan view of the safety indwelling syringe according to the second embodiment of this invention, showing the hollow needle housed in the protective sheath.
Figure 11:
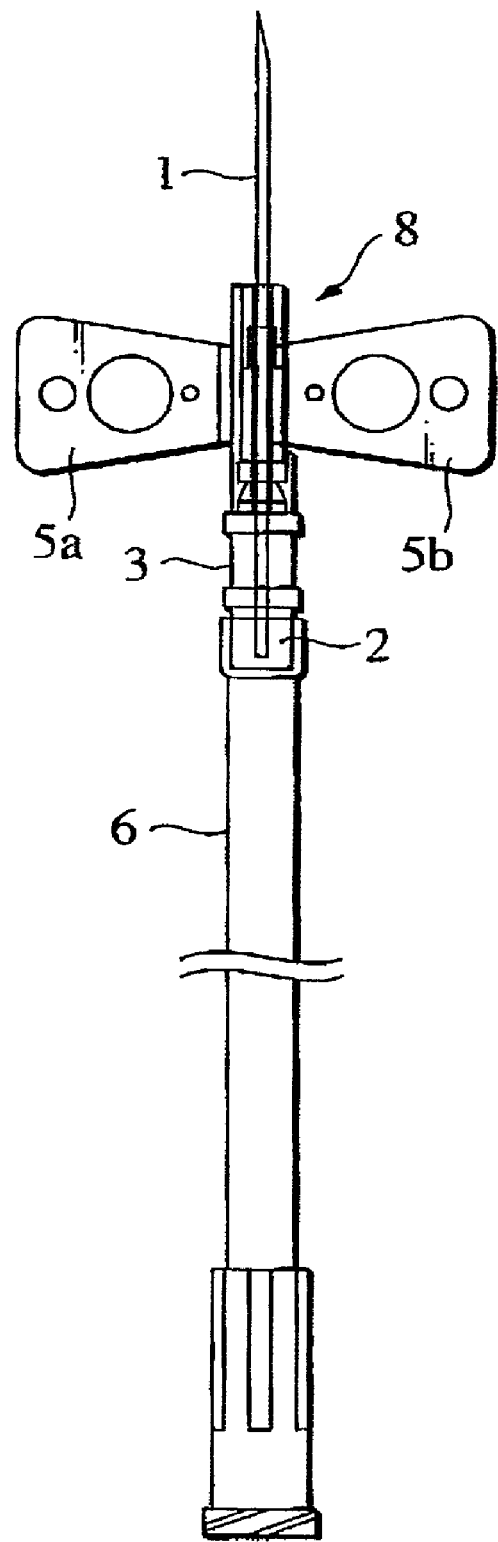
FIG. 11 is a plan view of the safety indwelling syringe according to the second embodiment of this invention, showing the hollow needle exposed for use.
Figure 12:
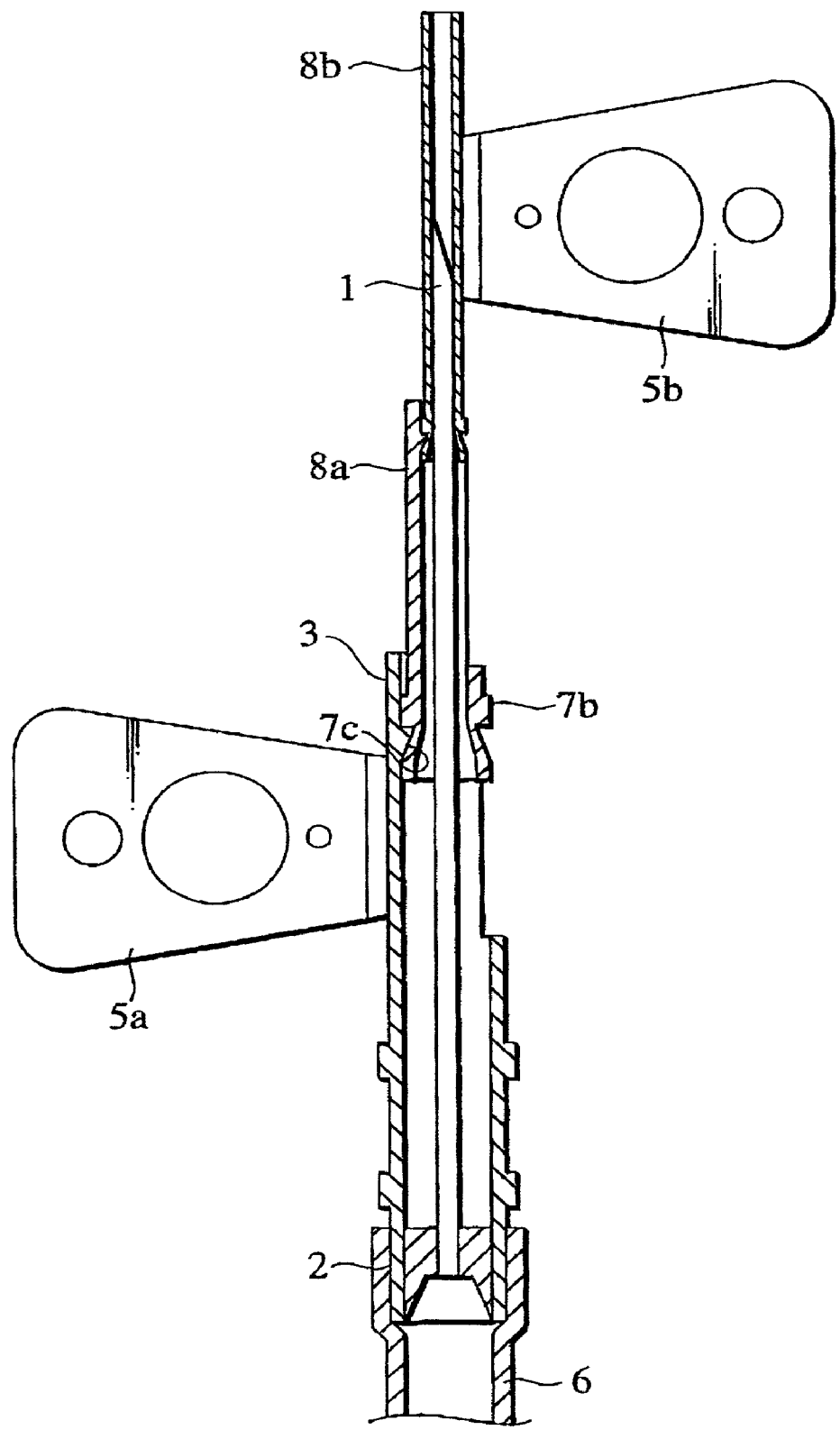
FIG. 12 is a plan view of the safety indwelling syringe according to the second embodiment of this invention, showing the hollow needle housed in the protective sheath.

The first slide sheath 8a has a slit 8a$_1$ corresponding to a slit 3a of the fixed sheath 3. The slits 3a and 8a$_1$ slidably house a proximal portion of a second wing 5b of the second slide sheath 8b as shown in FIG. 7. Thus the first and second slide sheaths 8a and 8b are compactly housed in the fixed sheath 3.

A third embodiment of this invention will be described with reference to FIGS. 13 to 18. Elements substantially identical to those in the first embodiment are referred to by the same numerals. Different elements are referred to by new numerals.

Figure 13:
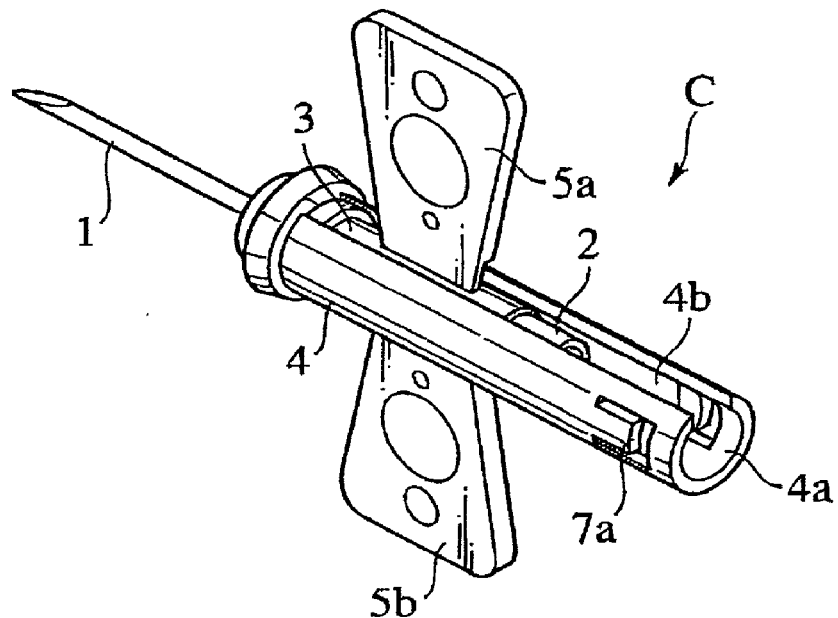
FIG. 13 is a perspective view of a safety indwelling syringe according to a third embodiment of this invention.
Figure 14:
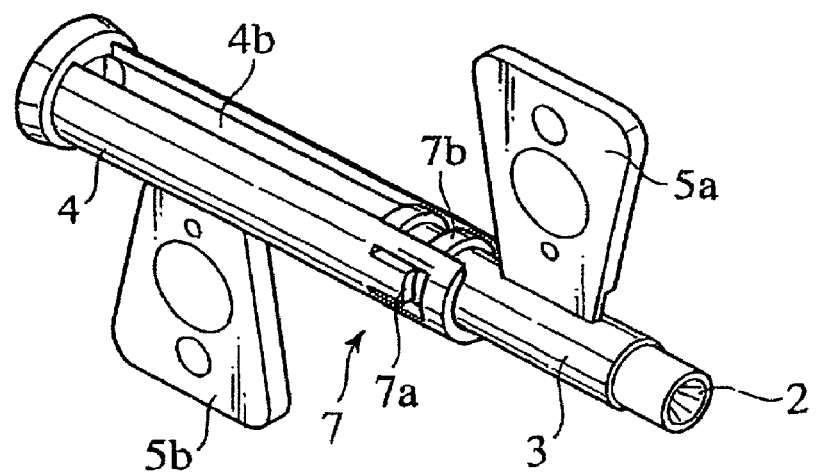
FIG. 14 is a perspective view of the safety indwelling syringe according to the third embodiment of this invention, showing a hollow needle housed in a protective sheath.

A safety indwelling syringe C according to the third embodiment of this invention has a protective sheath 4 slidably fitted onto the outside of a fixed sheath 3 as shown in FIGS. 13 and 14.

Figure 15:
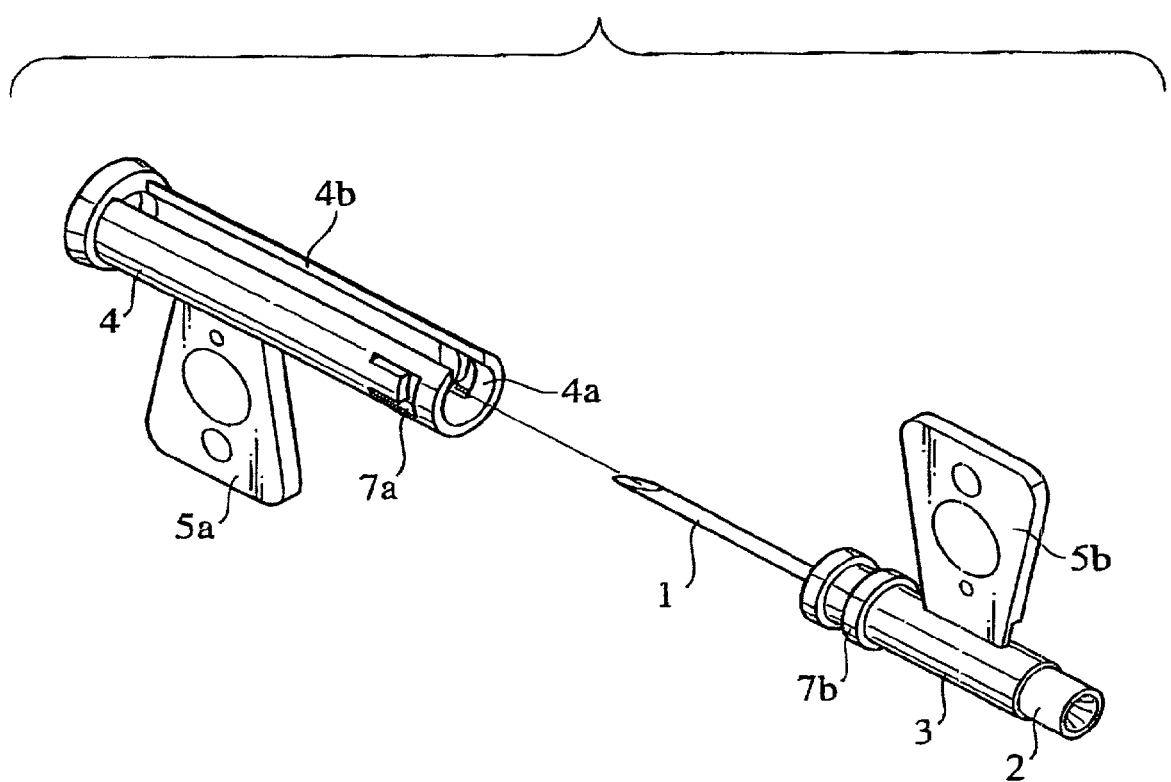
FIG. 15 is an exploded perspective view of the safety indwelling syringe according to the third embodiment of this invention.

The protective sheath 4 has a diameter greater than that of the fixed sheath 3, and has a slit 4b for housing a proximal portion of a first wing 5a protruded from the fixed sheath 3, a front opening 4a communicating with the slit 4b, and a locking slot 7a for engaging a locking projection 7b of the fixed sheath 3 as shown in FIG. 15.

Figure 18:
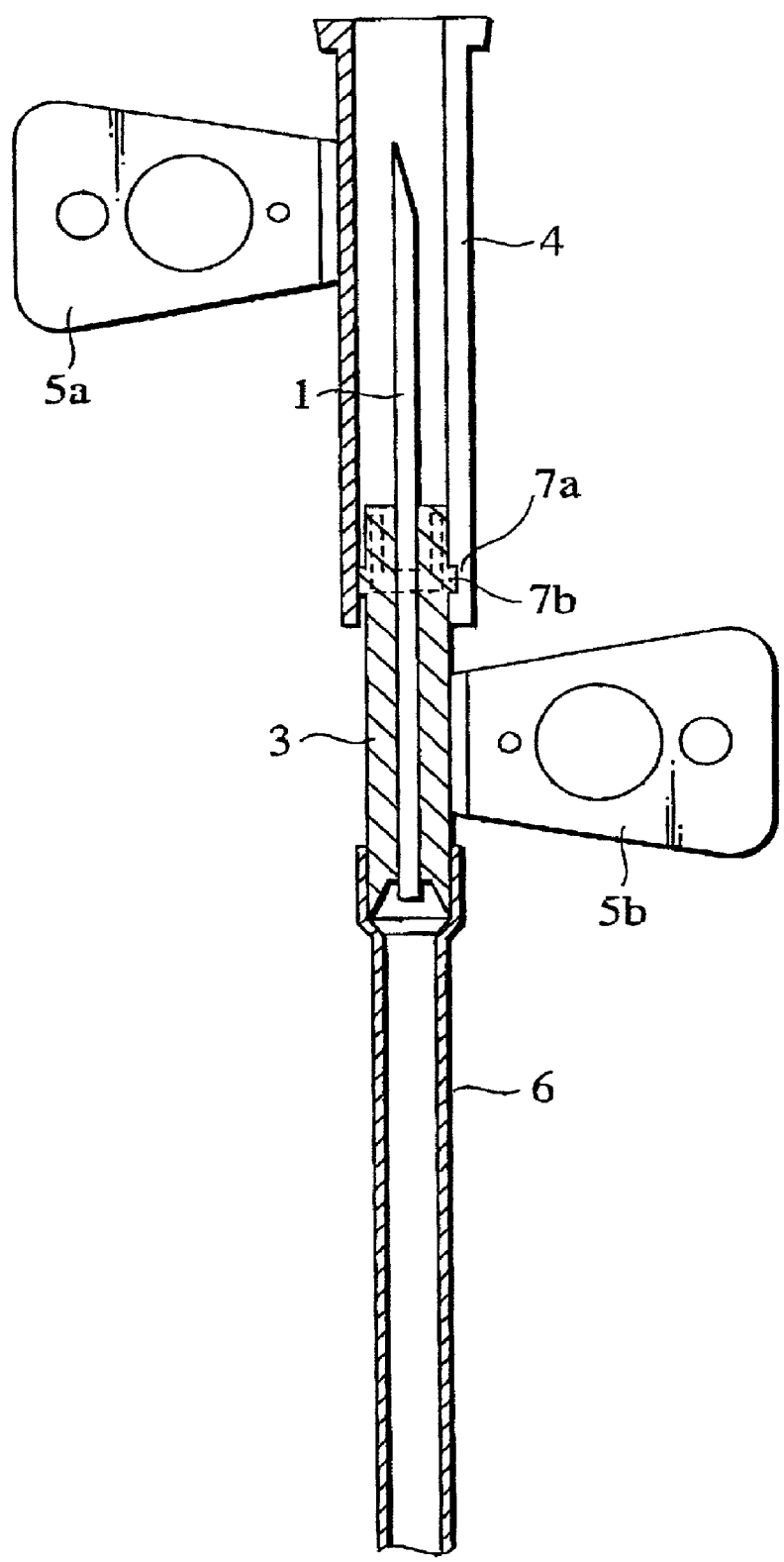
FIG. 18 is a plan view of the safety indwelling syringe according to the third embodiment of this invention, showing the hollow needle housed in the protective sheath.

When the protective sheath 4 is pulled forwardly or toward the tip of a hollow needle 1 to cover the needle 1, the locking slot 7a and the locking projection 7b are engaged with one another as shown in FIG. 18, preventing the sliding out of the protective sheath 4. Once housed in the protective sheath 4, the hollow needle 1 is not exposed until the engagement is intentionally released. This easily and reliably prevents accidentally sticking the needle 1 into a finger.

Figure 19:
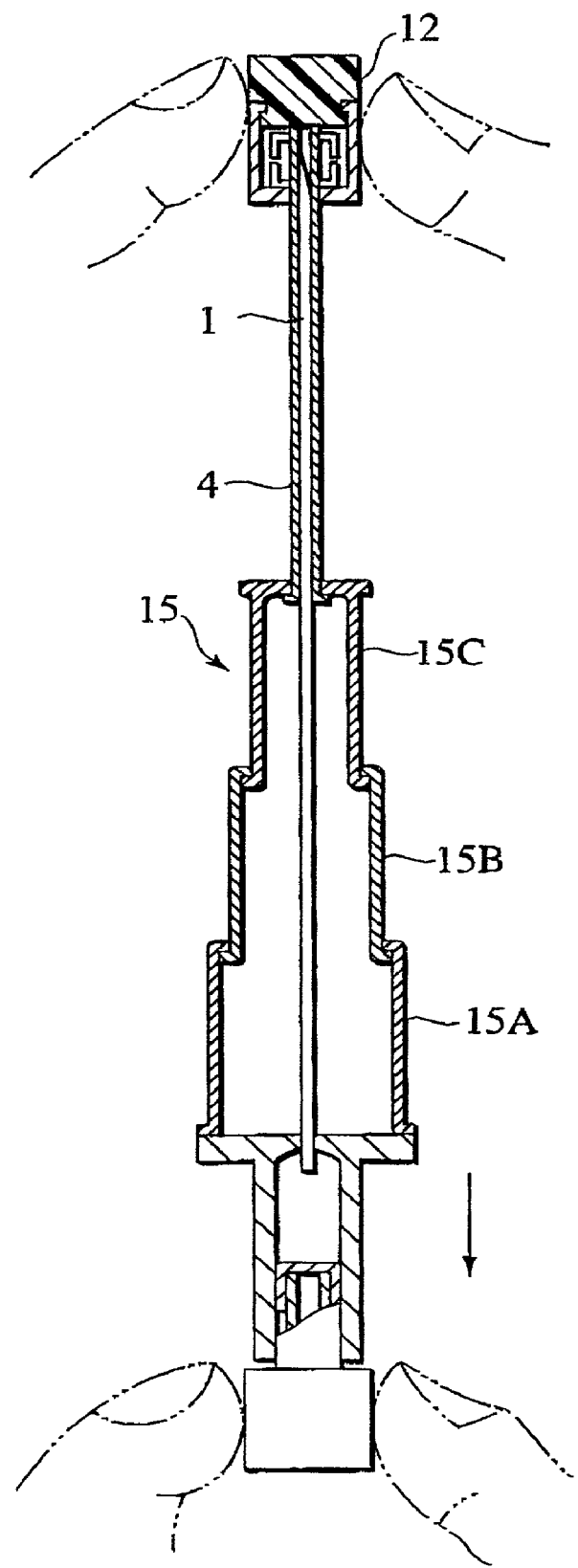
FIG. 19 is a longitudinal cross-sectional view of a safety indwelling syringe according to a fourth embodiment of this invention.

A fourth embodiment of this invention will be described with reference to FIGS. 19 to 20. Elements substantially identical to those in the first embodiment are referred to by the same numerals. Different elements are referred to by new numerals.

A safety indwelling syringe D according to the fourth embodiment of this invention has a telescopic sheath 15 consisting of three hollow circular cylinders 15A to 15C.

The telescopic sheath 15 is slidable like a telescope. A protective sheath 4 is engaged with a front end of the hollow cylinder 15c positioned at the front of the sheath 15, being prevented from slipping out.

Figure 20:
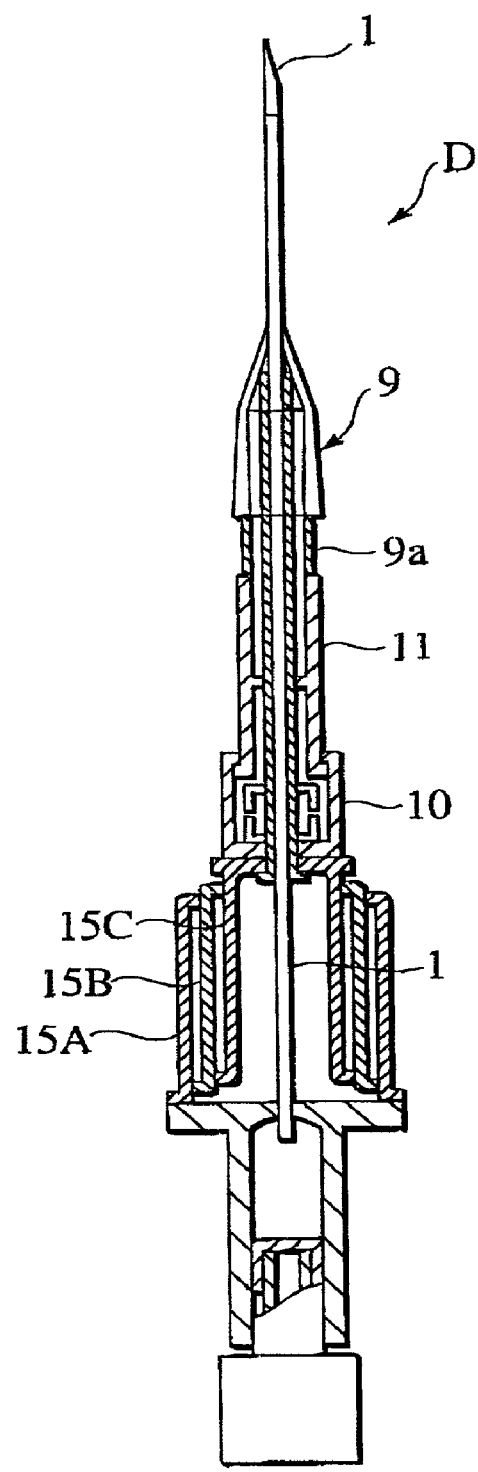
FIG. 20 is a longitudinal cross-sectional view of the safety indwelling syringe according to the fourth embodiment of this invention, showing a hollow needle exposed for use.

The safety indwelling syringe D of this embodiment is used in combination with a catheter 9 shown in FIG. 20. The protective sheath 4 has an elongated shape to be inserted into the catheter 9 for support. An adapter 10 is provided at a rear end of the protective sheath 4.

The adapter 10 is attached onto a connector 11 attached to a clamp 9a for fitting the catheter 9. When removed from the screw adapter 11, a front opening of the adapter 10 is closed by a rubber plug 12.

According to the safety indwelling syringe D of this embodiment, the adapter 10 always clamps the protective sheath 4. When the hollow needle 1 is pulled out from the catheter 9, the hollow cylinders 15B and 15C and the protective sheath 4 are pulled forwardly or toward the tip of the hollow needle 1. When the pulling out of the hollow needle 1 is finished, the hollow needle 1 is automatically housed in the protective sheath 4. This significantly prevents accidental sticking of the hollow needle 1 into a finger, which sometimes occurs when a conventional clamped catheter is used. This further eliminates a defect that a clamped portion of the conventional catheter is likely to flex.

Figure 21:
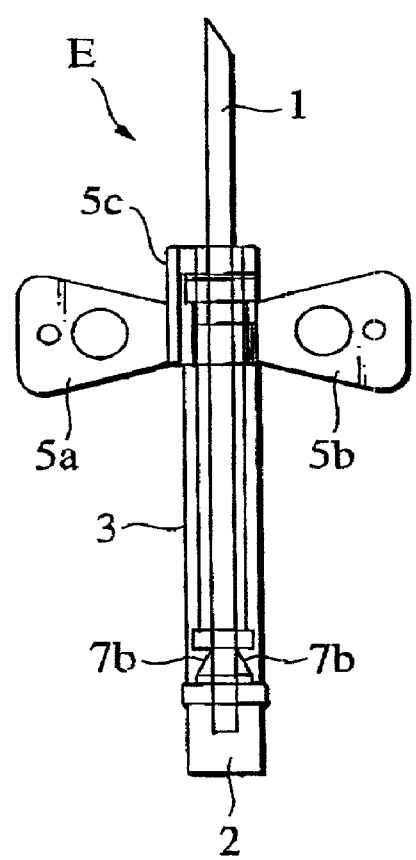
FIG. 21 is a plan view of a safety indwelling syringe according to a fifth embodiment of this invention.
Figure 22:
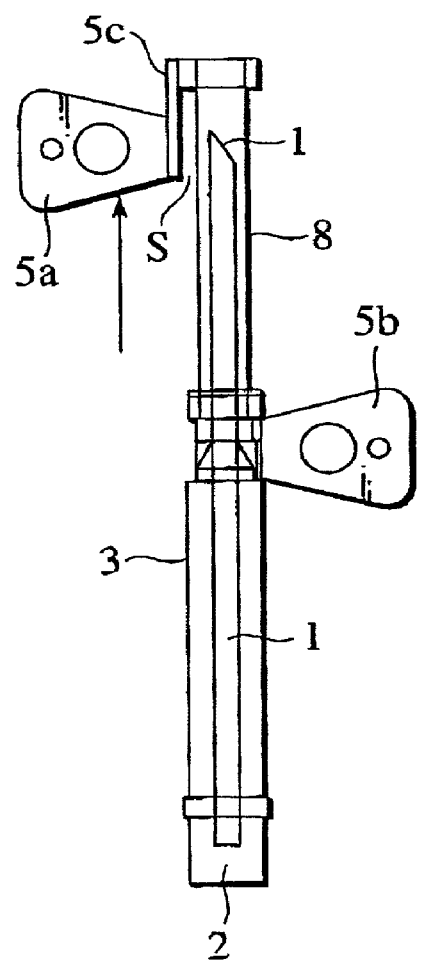
FIG. 22 is a plan view of the safety indwelling syringe according to the fifth embodiment of this invention, showing a hollow needle housed in a protective sheath.
Figure 23:
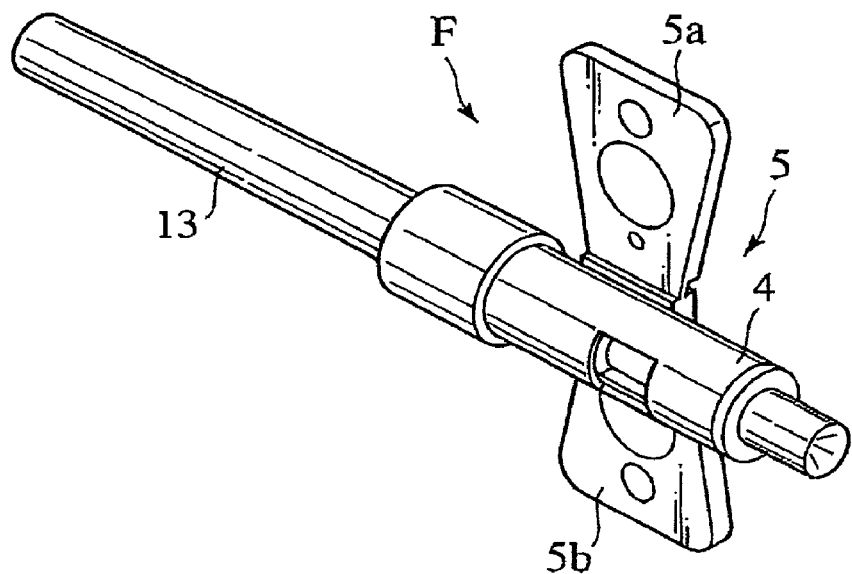
FIG. 23 is a perspective view of a safety indwelling syringe according to a sixth embodiment of this invention.
Figure 24:
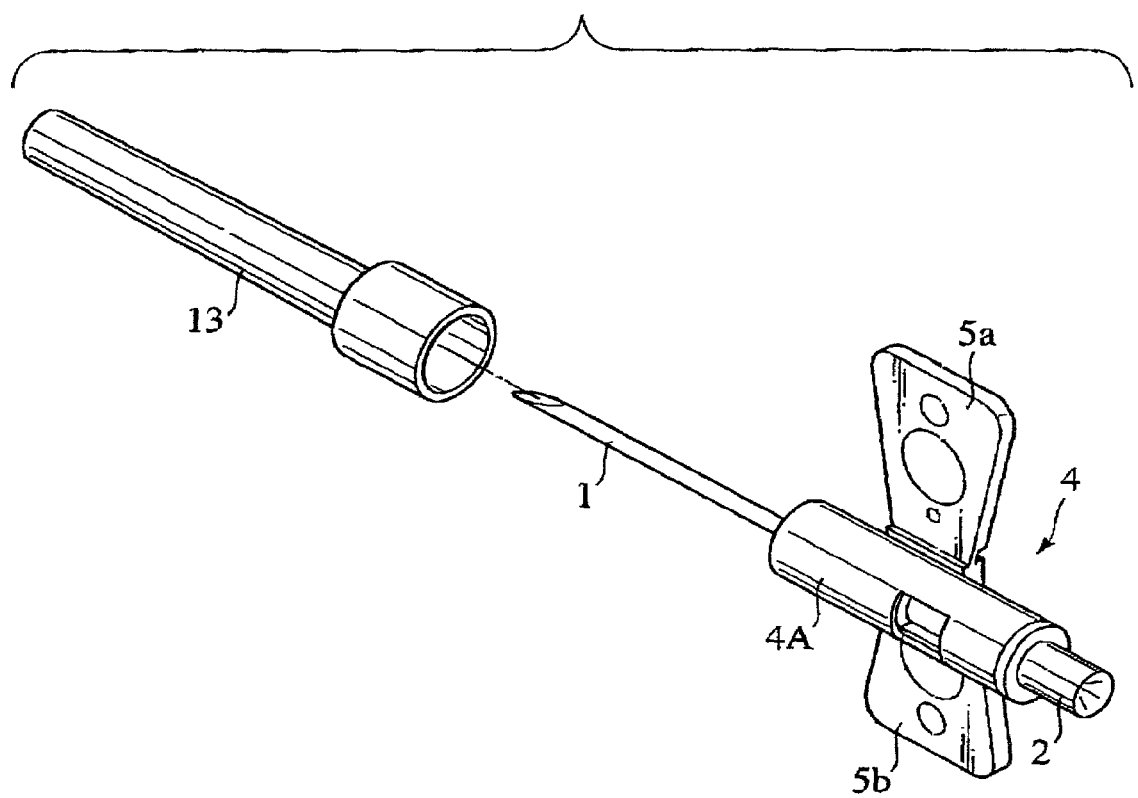
FIG. 24 is a perspective view of the safety indwelling syringe according to the sixth embodiment of this invention with a cap removed.

A fifth embodiment of this invention will be described with reference to FIGS. 21 and 22. Elements substantially identical to those in the first embodiment are referred to by the same numerals. Different elements are referred to by new numerals.

A safety indwelling syringe E according to the fifth embodiment of this invention has a slide sheath 8 having no slit, in contrast to the above-described embodiments. The slide sheath 8 has, as shown in FIG. 22, a mounting piece 5c to which a first wing 5a is attached.

A space S is provided between the mounting piece 5c and the slide sheath 8 for accommodating the thickness of a fixed sheath 3. The mounting piece 5c is detachably fitted onto a front portion of the slide sheath 8 in a straddling manner.

A locking projection 7b is protruded outside a proximal end of the slide sheath 8 and engages a locking slot 7a provided inside a front end of the fixed sheath 3.

When the first wing 5a and a second wing 5b are aligned symmetrically, a hollow needle 1 is exposed. When the first wing 5a is held with fingers to slide in a direction to distance the wing 5a from the second wing 5b, the slide sheath 8 is pulled out forward from the fixed sheath 3, covering the hollow needle 1. Such an easy operation makes the hollow needle 1 housed in the slide sheath 8, enabling safe disposal thereof.

A sixth embodiment of this invention will be described with reference to FIGS. 23 to 27. Elements substantially identical to those in the first embodiment are referred to by the same numerals. Different elements are referred to by new numerals.

A safety indwelling syringe F according to the sixth embodiment is different from the above-described embodiments in that a first wing 5a and a second wing 5b are integrally molded and fixed on an outer surface of a protective sheath 4.

Figure 25:
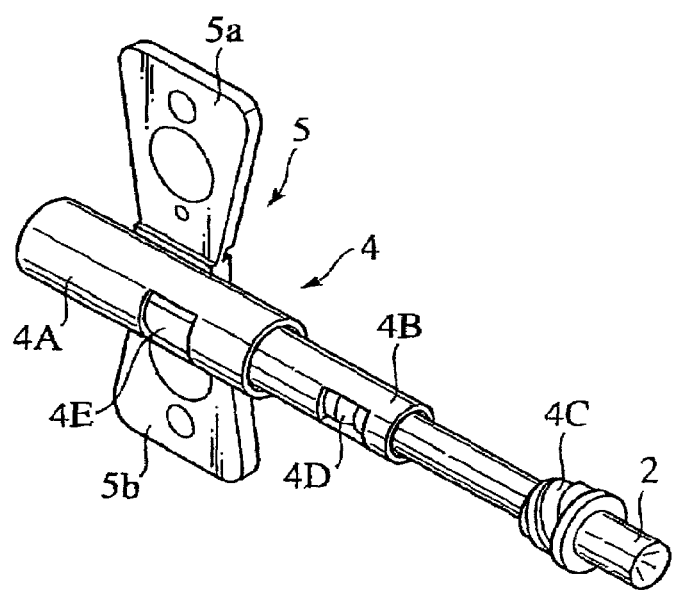
FIG. 25 is a perspective view of the safety indwelling syringe according to the sixth embodiment of this invention, showing a hollow needle housed in a protective sheath.
Figure 26:
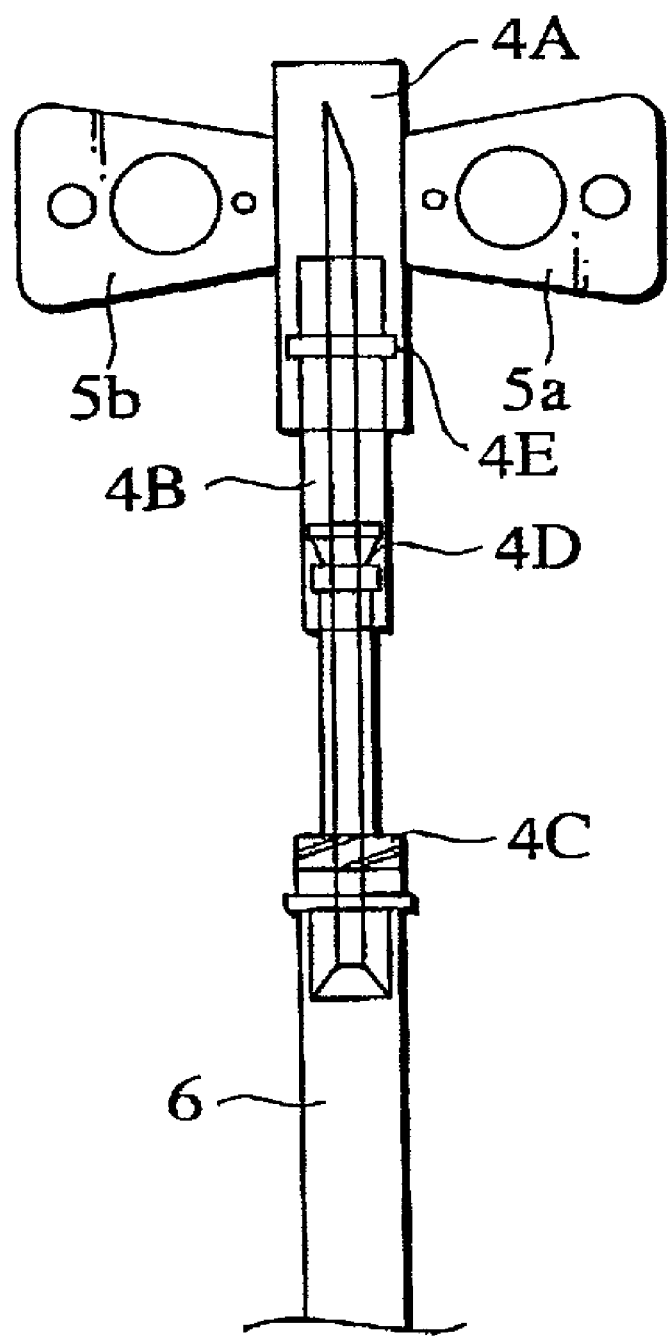
FIG. 26 is a plan view of the safety indwelling syringe according to the sixth embodiment of this invention, showing the hollow needle housed in the protective sheath.

As shown in FIG. 25, the protective sheath 4 consists of two slide sheaths 4A and 4B having different diameters. The slide sheath 4A with the paired wings 5 fixed thereon is slidably fitted onto the slide sheath 4B.

The protective sheath 4 has a first locking means 4C for engaging the slide sheath 4A with a hub 2, and second and third locking means 4D and 4E for retaining the protective sheath 4 in a position to cover a hollow needle 1. The first locking means 4C consists of a thread and a screw hole to be able to be disengaged. The second and third locking means 4D and 4E, once engaged, cannot be disengaged.

Figure 27:
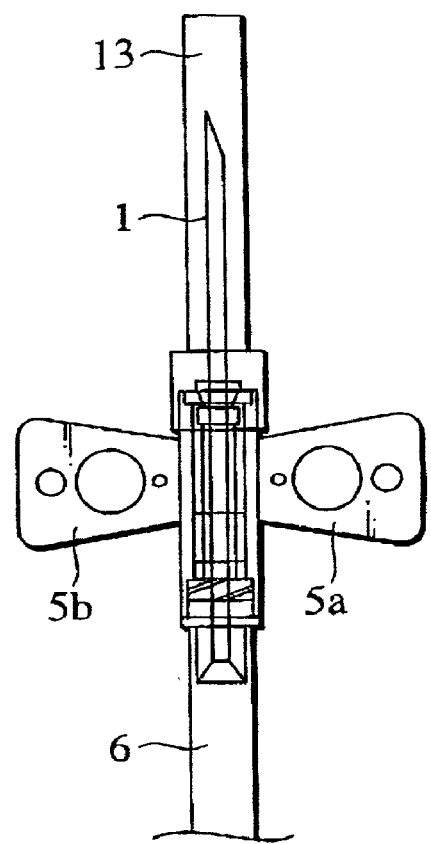
FIG. 27 is a plan view of the safety indwelling syringe according to the sixth embodiment of this invention before use.
Figure 28:
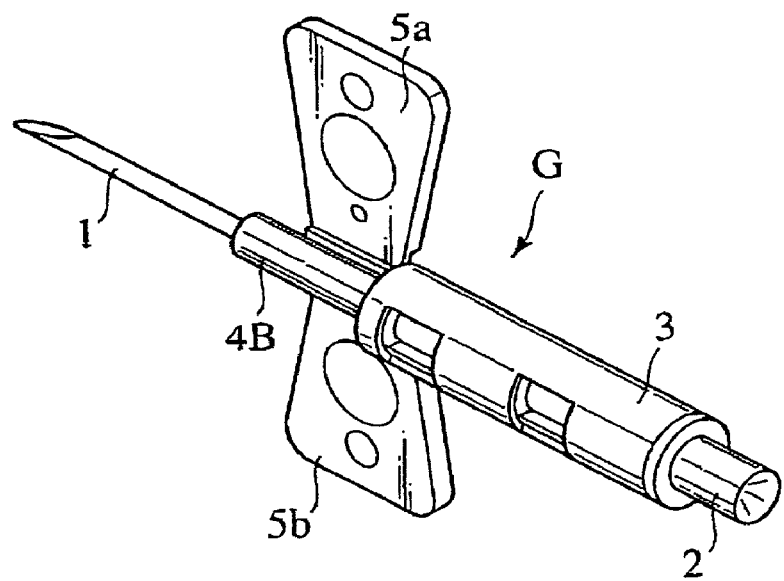
FIG. 28 is a perspective view of a safety indwelling syringe according to a seventh embodiment of this invention.
Figure 29:
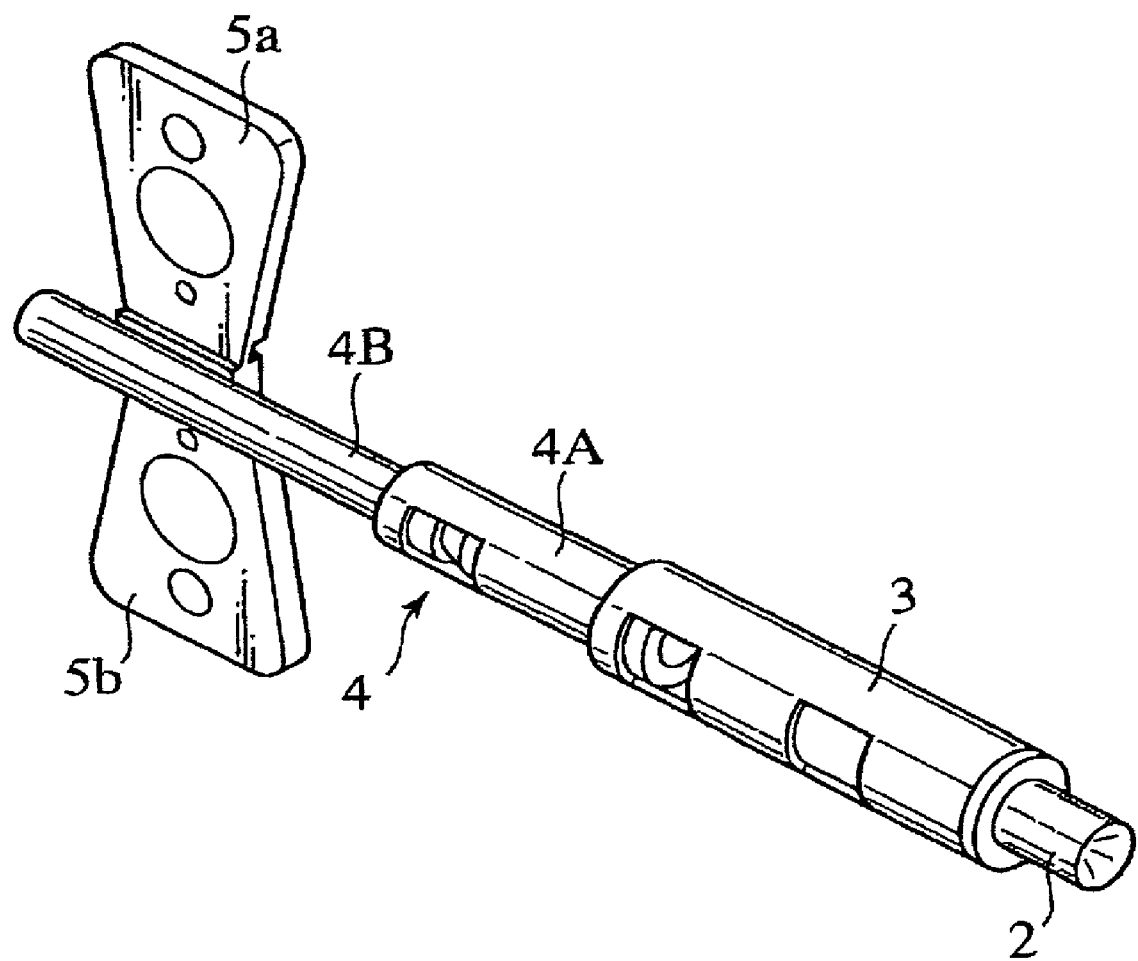
FIG. 29 is a perspective view of the safety indwelling syringe according to the seventh embodiment of this invention, showing a hollow needle housed in a protective sheath.
Figure 30:
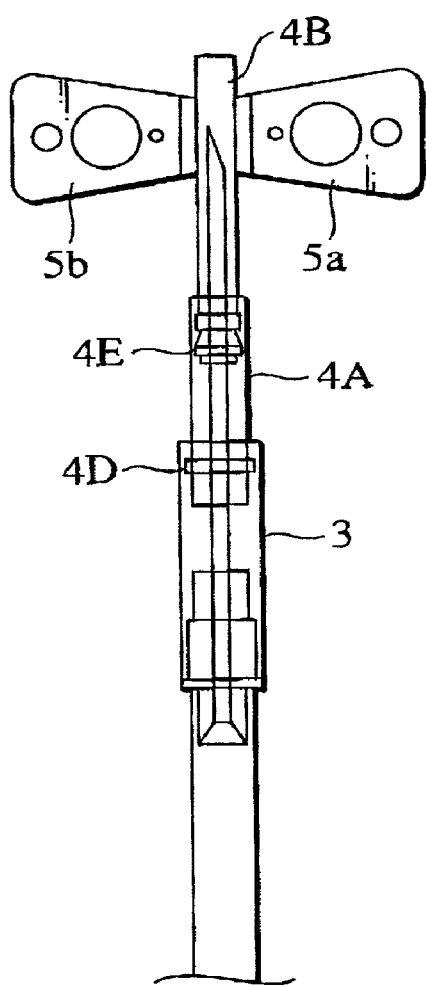
FIG. 30 is a plan view of the safety indwelling syringe according to the seventh embodiment of this inventions showing the hollow needle housed in the protective sheath.
Figure 31:
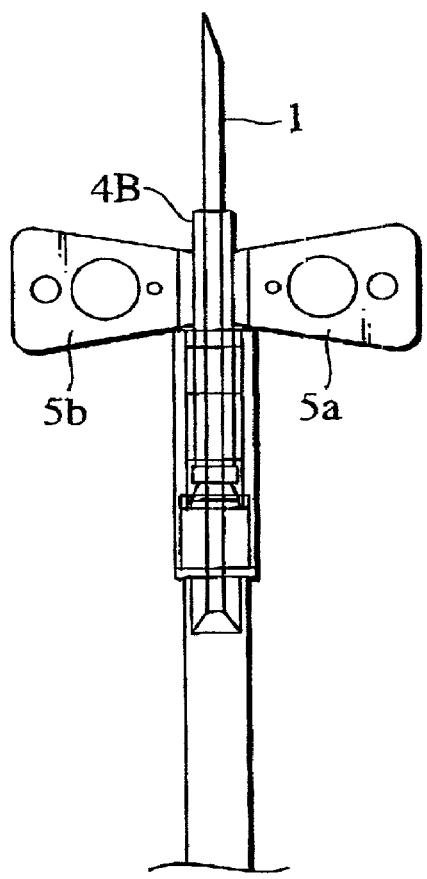
FIG. 31 is a plan view of the safety indwelling syringe according to the seventh embodiment of this invention, showing the hollow needle exposed.

The safety indwelling syringe F of this embodiment is supplied with the hollow needle 1 covered by a cap 13 as shown in FIG. 27. The cap 13 is removed for use. After use, the first slide sheath 4A is rotated to disengage the first locking means 4C, and then either of the wings 5a and 5b is held with fingers to be moved forward or toward the tip of the hollow needle 1. The first and second slide sheaths 4A and 4B are thus pulled forward to house the hollow needle 1, and the second and third locking means 4D and 4E are engaged without a possibility of disengagement, thereby enabling safe disposal.

A seventh embodiment of this invention will be described with reference to FIGS. 28 to 31. Elements substantially identical to those in the first embodiment are referred to by the same numerals. Different elements are referred to by new numerals.

A safety indwelling syringe G according to the seventh embodiment of this invention has a protective sheath 4 slidably fitted into a fixed sheath 3. The protective sheath 4 consists of two slide sheaths 4A and 4B having different diameters. The second slide sheath 4B is slidably fitted into the first slide sheath 4A. A pair of wings 5 is fixed on an outer surface of the second slide sheath 4B. The pair of wings 5 consists of a first wing 5a and a second wing 5b integrally molded.

The protective sheath 4 has second and third locking means 4D and 4E for retaining the protective sheath 4 in a position to cover a hollow needle 1. The second and third locking means 4D and 4E are designed not to be disengaged once engaged.

According to the safety indwelling syringe G of this embodiment, after use, either of the wings 5a and 5b is held with fingers to move forwardly or toward the tip of the hollow needle 1, pulling forward the first and second slide sheaths 4A and 4B, and thereby housing the hollow needle 1. At that time, the second and third locking means 4D and 4E are engaged without a possibility of disengagement, enabling safe disposal.

Although the invention has been described above by reference to certain embodiments of the invention, the invention is not limited to the embodiments described above. Modifications and variations of the embodiments described above will occur to those skilled in the art, in light of the above teachings.

What is claimed is:

1. A safety indwelling syringe, comprising:
   a hollow needle to be inserted into a body of a patient;
   a fixed sheath fixing the hollow needle and having a tubular portion, the tubular portion covering the needle partly;
   a protective sheath slidably fitted to and guided by the tubular portion of the fixed sheath, the protective sheath being movable relative to the tubular portion and covering the hollow needle entirely;
   the fixed sheath and the protective sheath comprising locking means having a slot and a latch projection for engaging with the slot so that the locking means prevents the protective sheath from separating from the fixed sheath; and
   a pair of wings, at least one of the wings being coupled to the protective sheath for pulling out the protective sheath.

2. A safety indwelling syringe as set forth in claim 1, wherein the fixed sheath includes a slit and the protective sheath includes a wing coupled thereto, the wing being movable along the slit until a portion of the wing contacts an end of the slit and stops further movement of the wing, and wherein the end of the slit and the locking means restrict sliding movement of the protective sheath in both directions.

3. A safety indwelling syringe as set forth in claim 1, wherein the protective sheath is slidably fitted inside the tubular portion of the fixed sheath.

4. A safety indwelling syringe as set forth in claim 1, wherein the protective sheath is slidably fitted outside the tubular portion of the fixed sheath.

5. A safety indwelling syringe as set forth in claim 1, wherein the protective sheath comprises at least two slide sheaths.

6. A safety indwelling syringe comprising:
   a hollow needle to be inserted into a body of a patient;
   a fixed sheath fixing the hollow needle and having a tubular portion, the tubular portion partially covering the needle; and
   a protective sheath slidably movable and guided by the tubular portion of the fixed sheath between a first position where the protective sheath is housed inside of the fixed sheath and a second position where a tip of the hollow needle is entirely covered by the protective sheath; wherein,
   the protective sheath and the tubular portion of the fixed sheath have a locking means for restricting sliding movement of the protective sheath relative to the tubular portion, wherein the locking means comprises a locking slot and a locking projection, and
   wherein:
   each of the fixed sheath and the protective sheath has a wing, and when the wings are aligned symmetrically, the hollow needle is exposed, and when the sheaths are slid in directions to distance the wings from one another and locked, the protective sheath covers the hollow needle entirely.

7. A safety indwelling syringe, comprising:
   a hollow needle to be inserted into a body of a patient;
   a fixed sheath fixing the hollow needle and having a tubular portion, the tubular portion partially covering the needle; and
   a protective sheath slidably movable and guided by the tubular portion of the fixed sheath between a first position where the protective sheath is housed inside of the fixed sheath and a second position where a tip of the hollow needle is entirely covered by the protective sheath; wherein,
   the protective sheath and the tubular portion of the fixed sheath have a locking means for restricting sliding movement of the protective sheath relative to the tubular portion, and
   wherein the fixed sheath includes a slit and the protective sheath includes a wing coupled thereto, the wing being movable along the slit until a portion of the wing contacts an end of the slit and stops further movement of the wing, and wherein the end of the slit and the locking means restrict sliding movement of the protective sheath in both directions.

* * * * *